(12) United States Patent
Marchitto et al.

(10) Patent No.: US 6,889,075 B2
(45) Date of Patent: **\*May 3, 2005**

(54) OPTICAL IMAGING OF SUBSURFACE ANATOMICAL STRUCTURES AND BIOMOLECULES

(75) Inventors: Kevin S. Marchitto, Mt. Eliza (AU); Stephen T. Flock, Mt. Eliza (AU)

(73) Assignee: Rocky Mountain Biosystems, Inc., Golden, CO (US)

(\*) Notice: Subject to any disclaimer, the term of this patent is extended or adjusted under 35 U.S.C. 154(b) by 460 days.

This patent is subject to a terminal disclaimer.

(21) Appl. No.: 09/848,596

(22) Filed: May 3, 2001

(65) Prior Publication Data

US 2002/0016533 A1 Feb. 7, 2002

Related U.S. Application Data

(60) Provisional application No. 60/201,592, filed on May 3, 2000, now abandoned.

(51) Int. Cl.[7] ................................................ A61B 5/00
(52) U.S. Cl. ...................................... 600/473; 600/476
(58) Field of Search ................................ 600/310, 473, 600/475, 476, 477, 431; 424/9.1

(56) References Cited

U.S. PATENT DOCUMENTS

| | | | |
|---|---|---|---|
| 4,907,876 A | 3/1990 | Suzuki et al. | 356/41 |
| 4,934,372 A | 6/1990 | Corenman et al. | 128/633 |
| 5,291,885 A | 3/1994 | Taniji et al. | 128/633 |
| 5,606,969 A | 3/1997 | Butler et al. | 128/653.1 |
| 5,615,673 A | 4/1997 | Berger et al. | 128/633 |
| 5,788,639 A | 8/1998 | Zavislan et al. | 600/476 |
| 5,976,502 A | 11/1999 | Khoobehi et al. | 424/9.6 |
| 6,032,070 A * | 2/2000 | Flock et al. | 600/473 |
| 6,178,340 B1 * | 1/2001 | Svetliza | 600/310 |
| 6,230,046 B1 * | 5/2001 | Crane et al. | 600/476 |
| 6,272,374 B1 * | 8/2001 | Flock et al. | 600/473 |
| 6,353,753 B1 * | 3/2002 | Flock et al. | 600/473 |
| 2001/0027273 A1 * | 10/2001 | Flock et al. | 600/473 |

\* cited by examiner

*Primary Examiner*—Eleni Mantis Mercader
(74) *Attorney, Agent, or Firm*—Benjamin Aaron Adler

(57) ABSTRACT

The present invention provides various methods/systems of optical imaging of subsurface anatomical structures and biomolecules utilizing red and infrared radiant energy. Also provided are various applications of such methods/systems in medical diagnosis and treatment.

7 Claims, 11 Drawing Sheets

OPTICAL IMAGING OF SUBSURFACE ANATOMICAL STRUCTURES AND BIOMOLECULES

CROSS-REFERENCE TO RELATED APPLICATION

This non-provisional patent application claims benefit of provisional patent application U.S. Ser. No. 60/201,592, filed May 3, 2000, now abandoned.

BACKGROUND OF THE INVENTION

1. Field of the Invention

The present invention relates generally to the fields of optical imaging and medical diagnosis. More specifically, the present invention relates to advanced methods of optical imaging of subsurface anatomical structures and biomolecules.

2. Description of the Related Art

The importance of imaging structures and biomolecules in humans is self-evident. Recently, many groups of investigators have been trying to develop optical imaging techniques in order to supercede, or reduce the requirements of using expensive and potentially harmful techniques including x-rays, ultrasound or magnetic and radio-frequency fields. Optical imaging techniques employing non-ionizing electromagnetic radiation are not harmful to biological tissue, and so are less hazardous and thus less expensive. However, there is a major limitation in using ultraviolet, visible and infrared radiant electromagnetic energy for imaging in that most tissues are highly scattering, and often strongly absorbing to such photons.

Nevertheless, infrared radiant energy is useful in non-invasive imaging of anatomical structures since it is relatively penetrating in tissue; the wavelengths of radiant energy from about 600 nm to about 1100 nm penetrates tissue quite well, when compared to visible, ultraviolet, or mid- to far infrared radiant energy. Furthermore, biomolecules exhibit absorption features in this red to near-infrared region of the spectrum due to electronic and vibrational/rotational absorption.

The prior art is deficient in the lack of effective means of imaging subsurface anatomical structures and biomolecules by using red and infrared radiant energy. The present invention fulfills this long-standing need and desire in the art.

SUMMARY OF THE INVENTION

The present invention provides various methods/systems of optical imaging of subsurface anatomical structures and biomolecules utilizing red and infrared radiant energy. Such methods enhance contrast in medical imaging, and are generally useful in non-invasive and relatively low cost imaging instruments. The techniques used include pulsatile enhanced imaging, confocal enhanced imaging, Raman enhanced imaging, laser speckle enhanced imaging, multiphoton interaction enhanced imaging, optical coherence tomography enhanced imaging, time correlated single photon counting enhanced imaging, and polarization enhanced imaging.

The present invention also provides a method of enhancing vascular contrast for imaging, comprising the step of applying the system disclosed herein in combination with the usage of exogenous chromophores or a range of other molecules which have tendency of concentrating in the tissue of interest.

Still provided is a method of detecting a disease in a subject, comprising the steps of applying the system disclosed herein to the subject to obtain an optical image, and then comparing the image with a control image obtained from a normal subject, wherein any difference between the two images is indicative of a possibility of having a disease in the test subject.

Further provided is a method of treating a subject having a disease, or further monitoring the treatment, by applying to the subject with the system disclosed herein in combination with the administration of therapeutic agents including laser energy.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 7C–F make use of an active device called a photoelastic modulator which can be used in the creation and analysis of polarized radiant energy.

DETAILED DESCRIPTION OF THE INVENTION

Figure 1A:
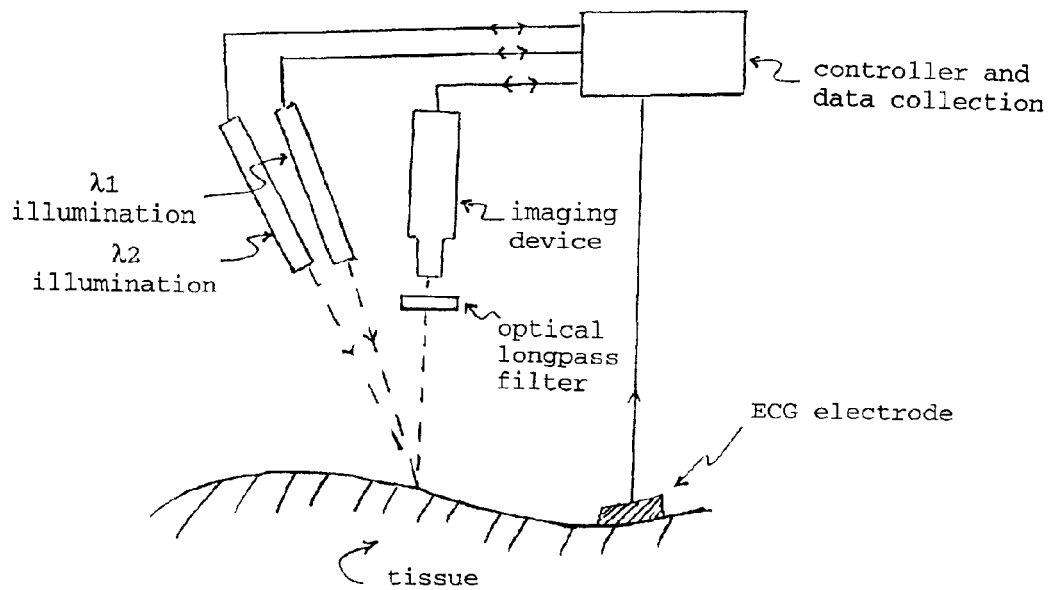
FIG. 1A shows a dual wavelength illumination device optionally employing an electrode to synchronize the video imaging with the pulse rate.

The present invention is directed to various methods/systems of optical imaging of subsurface anatomical structures and biomolecules utilizing red and infrared radiant energy. Such methods enhance contrast in medical imaging, and are generally useful in non-invasive and relatively low cost imaging instruments.

In one embodiment of the present invention, there is provided a method/system of enhancing optical imaging of an anatomical structure or a biomolecule utilizing one or more techniques selected from the group consisting of pulsatile enhanced imaging, confocal enhanced imaging, Raman enhanced imaging, laser speckle enhanced imaging, multiphoton interaction enhanced imaging, optical coherence tomography enhanced imaging, time correlated single photon counting enhanced imaging, and polarization enhanced imaging.

In another embodiment of the present invention, there is provided a method of enhancing vascular contrast for imaging, comprising the step of applying the system disclosed herein in combination with the usage of exogenous chromophores or a range of other molecules which have tendency of concentrating in the tissue of interest.

In still another embodiment of the present invention, there is provided a method of detecting a disease in a subject, comprising the steps of applying the system disclosed herein to the subject to obtain an optical image, and then comparing the image with a control image obtained from a normal subject, wherein any difference between the two images is indicative of a possibility of having a disease in the test subject.

In yet another embodiment of the present invention, there is provided a method of treating a subject having a disease, or further monitoring the treatment, by applying to the subject with the system disclosed herein in combination with the administration of therapeutic agents including laser energy.

The following examples are given for the purpose of illustrating various embodiments of the invention and are not meant to limit the present invention in any fashion.

EXAMPLE 1

Pulsatile Enhanced Imaging

Pulse oximeters are relatively common devices used to measure the percent oxygen saturation of blood, wherein red ($\lambda_1 \approx 660$ nm) and near infrared ($\lambda_2 \approx 940$ nm) radiant energy are passed through tissue (typically the fingertip). Using this device, it is possible to obtain a measurement of oxygen saturation of the blood based on the relative signals transmitted through the fingertips at each wavelength, knowing the absorption characteristics of the pertinent absorbing chromophores (tissue, oxygenated hemoglobin or $HbO_2$, deoxygenated hemoglobin or Hb), and after extensive calibration of the device with a direct measurement of blood oxygenation. One important operating characteristic that makes the pulse-oximeters useful is that they can discern between arterial and non-arterial absorption by discriminating between time-varying signals (due to the heart pumping and more evident in arterial blood) and non-varying signals (venous blood and tissue).

FIG. 1 shows an imaging device (e.g. charge-coupled device or CCD video camera, or vidicon) used to visualize an anatomic structure or region of interest that employs concepts used in pulse oximetry. The illuminating light consists of alternating pulses of radiant energy produced by, for example, light-emitting diodes (LEDs) filtered with a bandpass filter, or diode lasers, to produce radiant energy impinging on the surface with a wavelength of, for example, $\lambda_1=660$ and $\lambda_1=940$ nm. The detector captures an image, for example, every $\frac{1}{30}^{th}$ of a second, and so the illuminating light is alternately pulsed once every $\frac{1}{30}^{th}$ second. The images captured can be analyzed mathematically similar to standard transillumination pulse-oximeters except in this case reflectance, R, is measured, and not transmittance, T. The mathematical analysis is similar when one considers that optical density, OD, is related to R by $OD=-Log(R)$ and $T=1-R$. In a fashion similar to pulse oximetry, the signal can be decomposed into an time-varying signal (AC) and steady state (DC) signal, whereby the former is due to absorption within arteries (and to a much lesser degree, veins) while the latter is primarily due to non-arterial absorption.

Alternatively, an electrocardiogram (ECG) electrode could be used to monitor the heartbeat in order to match the phase of the signal with the heartbeat, thus achieving the same aforementioned result. In any case, this methodology would allow one to optically differentiate arterial blood absorption from absorption due to other biomolecular species, such as deoxygenated blood. Furthermore, it could optionally be used to measure blood oxygen saturation, which when combined with the imaging information, provides useful diagnostic information.

Figure 1B:
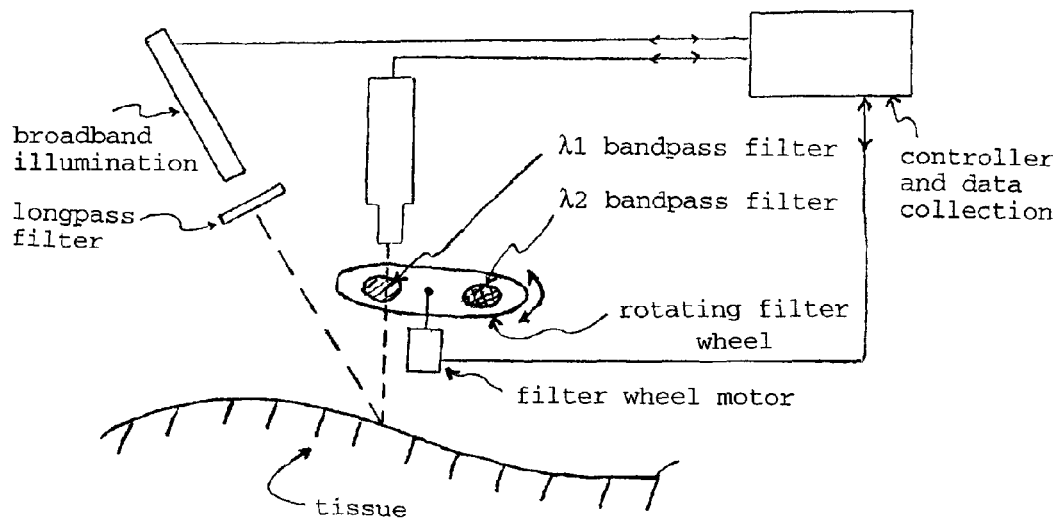
FIG. 1B shows a method for imaging in multiple wavelengths whereupon optical filters are sequentially inserted into the image axis at a rate which is synchronized with the video capture rate.

Another way to obtain sequential images at different wavelengths is to use a rotating filter wheel in front of the camera and a single broadband illumination source that produces radiant energy at both the necessary wavelengths, $\lambda_1$ and $\lambda_2$ (FIG. 1B). The rotation rate and phase of the optical filter wheel could be adjusted to maximize the AC signal (and thus would be in phase with the pulsatile arterial flow), or could be controlled by a pulse rate signal from an optional ECG electrode.

The aforementioned discussion of using multiple wavelengths of radiant energy to achieve imaging contrast can be used in a similar fashion to provide contrast between vessels and tissue and/or hemoglobin within blood vessels versus extravascular hemoglobin. Myoglobin (Mb) is a form of hemoglobin that transports oxygen in muscles and which provides much of the visual appearance of color in muscles. The absorption spectrum of myoglobin is different from oxy- and deoxyhemoglobin. This difference can be used to differentiate hemoglobin contained within vessels from myoglobin in vessel walls, muscle or other tissue, thus producing good blood-tissue contrast. Note that extravascular blood will not optically change in a pulsatile fashion as will blood in arteries (and to a lesser extent, veins), thus the aforementioned pulsatile imaging scheme can be used to differentiate intervascular blood from extravascular blood.

EXAMPLE 2

Confocal Enhanced Imaging

The concept of rejecting light scattered from locations other than the point being imaged (that is, with coordinates x,y,z), by using apertures in the imaging system, is referred to as confocal imaging. This concept has been used to "optically section" microscopic specimens being viewed with a microscope. Confocal microscopy normally uses white light illumination, or ultraviolet to green illumination to induce fluorescence in the sample. The former illumination results in significant chromatic aberrations in the final image, while the latter provides only a fluorescent image.

Figure 2:
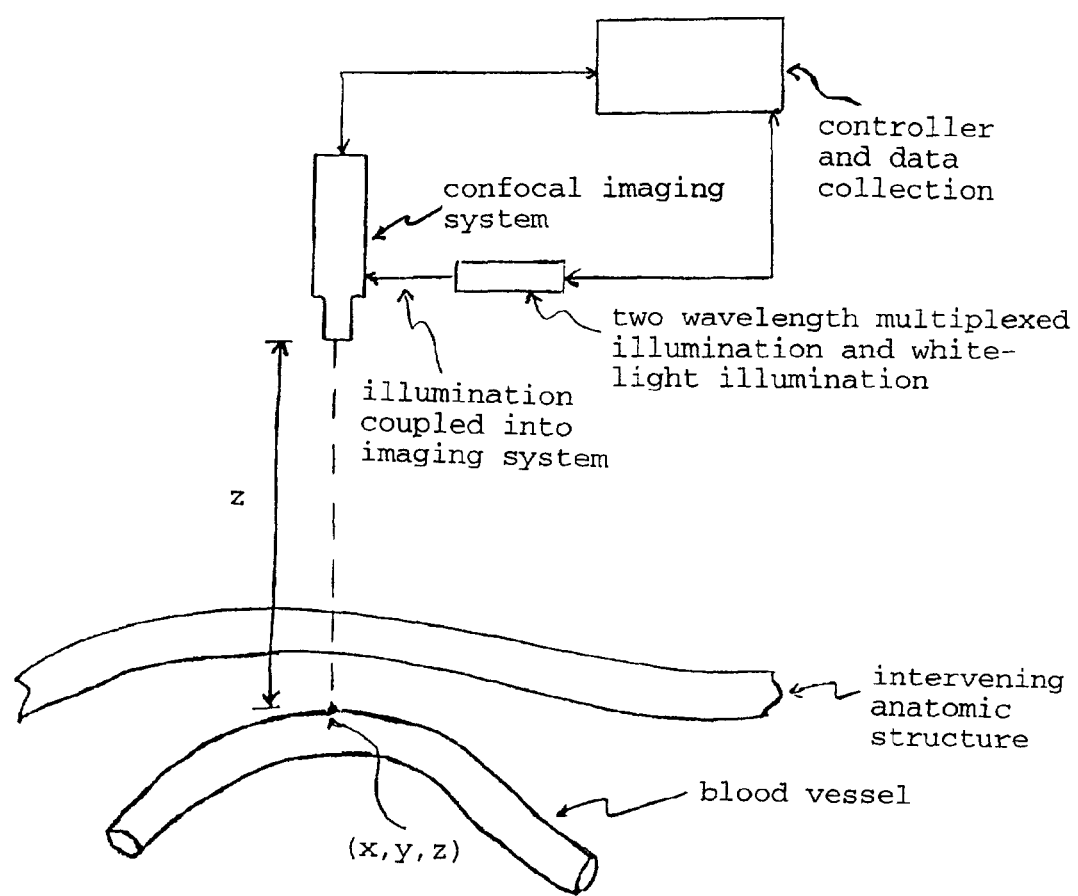
FIG. 2 shows a confocal imaging device whereby white light illumination and optionally infrared illumination and/or white light illumination are used to image subsurface blood vessels.

It would be beneficial, in certain cases, to use red and/or near infrared radiant energy in a confocal imaging optical system, along with white-light illumination. Narrow band illumination through the use of diode lasers or bandpass filtered broadband light sources would be optimal (FIG. 2). By alternately illuminating the region-of-interest (ROI), for example, 660 nm and 940 nm radiant energy in a confocal imaging system, it would be possible to collect information on $HbO_2$ and Hb as well as information as a function of depth in the sample. Illumination at these wavelengths could be alternated with illumination using white light so that a normally appearing image of the region-of-interest would also result. This could allow one to visualize blood vessels, for example, below other normally appearing intervening structures that reduce or eliminate the ability to visualize the vessels.

EXAMPLE 3
Raman Enhanced Imaging

Raman spectroscopy is a light scattering technique that uses (typically) laser radiation to excite the sample, whereby the scattered radiation emitted by the sample is analyzed. Emission data has two main characteristics: the frequencies at which the sample emits the radiation (a small number of the incident photons, perhaps only 1 in $10^6$, is emitted at frequencies different from that of the incident light), and the intensities of the emissions. Determining the frequencies allows identification of the sample's molecular makeup, since chemical functional groups are known to emit specific frequencies and emission intensity is related to the amount of the analyte present. Now, with highly sensitive imaging light detectors (e.g. CCDs) and efficient optics such as transmission holographic gratings and notch filters, Raman spectroscopy has seen a resurgence of interest in the medical field.

Figure 3:
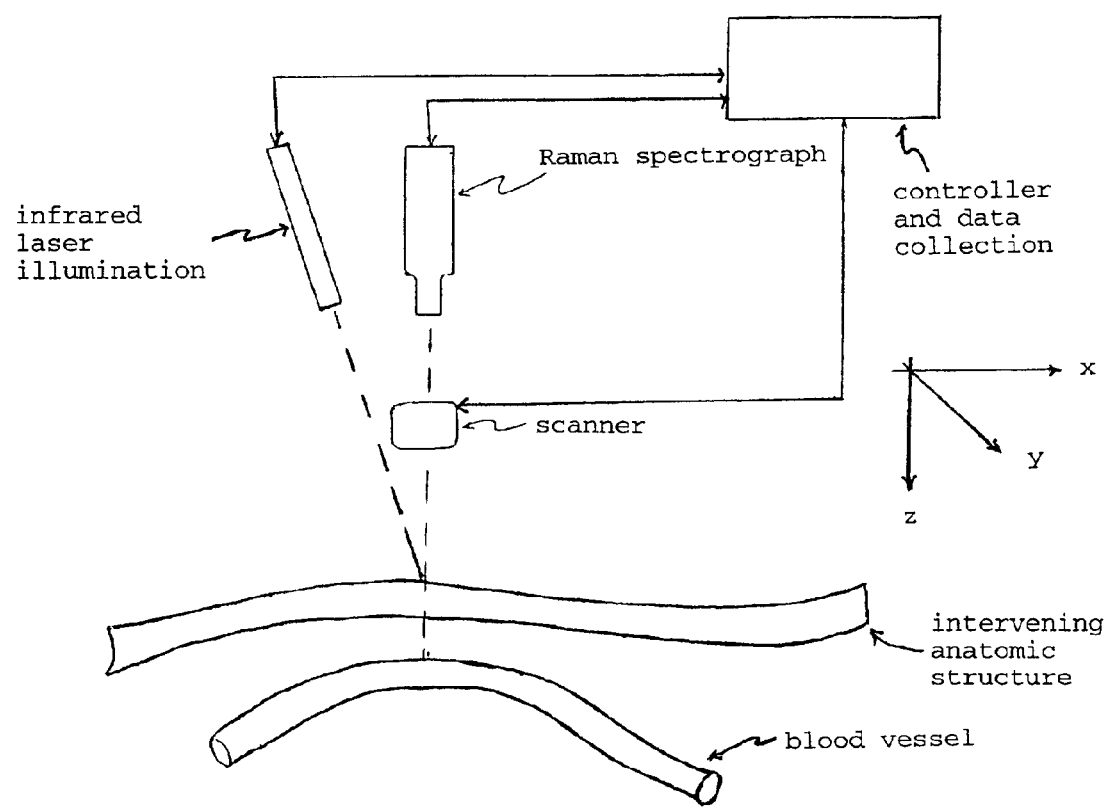
FIG. 3 shows an imaging system employing Raman scattered photons and a scanner positioned in front of the spectrograph optical system or the infrared laser illumination.

It would be useful to illuminate the anatomic structure of interest with the radiant energy produced by, for example, a 850 nm diode laser, and to use a Raman spectrograph for imaging (FIG. 3). The Raman scattered photons specific to Hb and/or $HbO_2$ could then be used to detect and discriminate blood from other tissues made of different biomolecules. Of course, the same idea can be extended to other biomolecular species of interest such as circulating pharmaceuticals, liver enzymes and glucose. To build up an image using Raman scattered photons, it may be necessary to either scan the collimated and focused illuminating light beam in a raster-scan, for example, and capture information point-by-point so that a two-dimensional image can be made up. Alternatively, the detector (if it is not an imaging type) can be scanned. Still alternatively, a two-dimensional imaging detector, such as a CCD, can be used. In any case, the strong molecular specificity of Raman scattering would allow for good rejection of signals not pertaining to the molecule of interest.

EXAMPLE 4
Laser Speckle Enhanced Imaging

Figure 4:
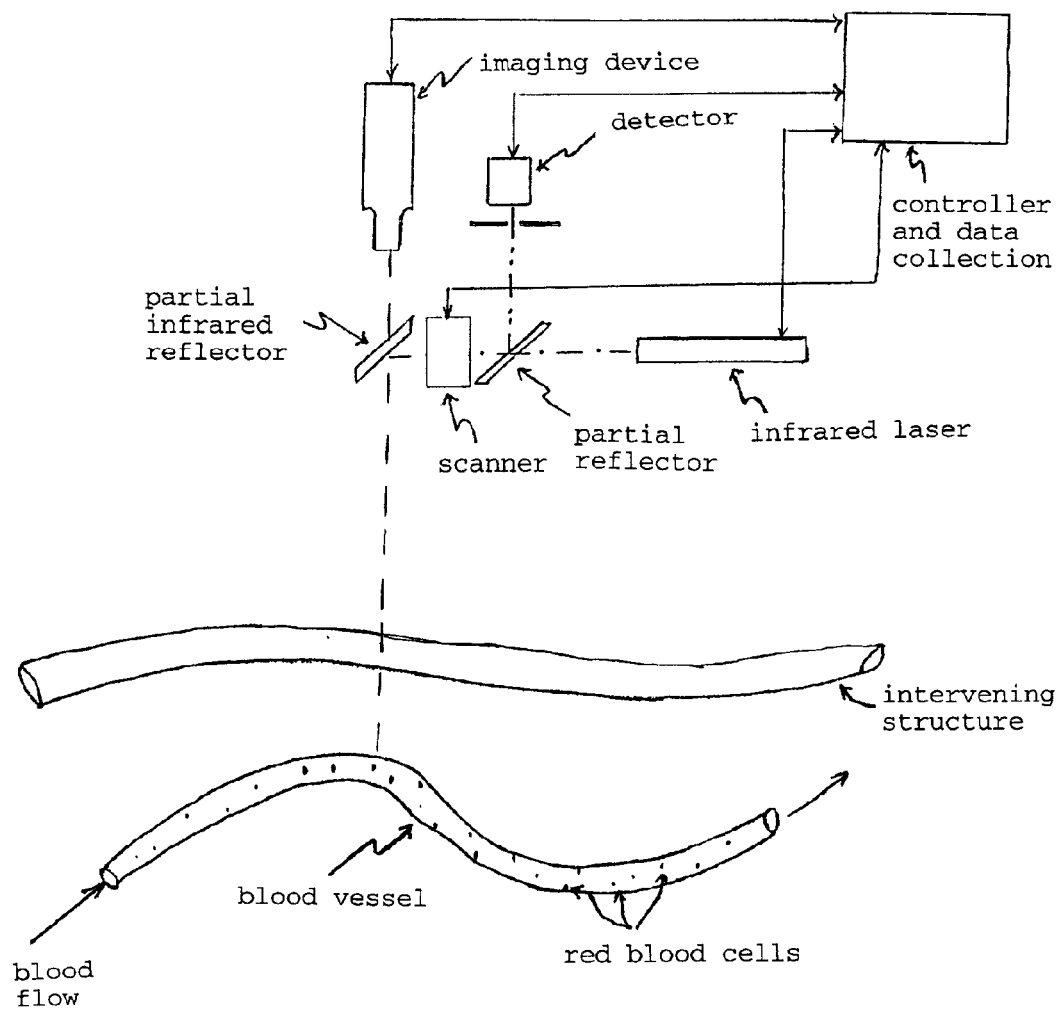
FIG. 4 shows a blood vessel imaging device where motion detection is employed.

If the movement and/or texture of objects reflecting coherent laser radiant energy have dimensions on the order of the wavelength of the radiant energy, then constructive and destructive interference can take place. To the eye, this can give the appearance of a "speckle" pattern superimposed on the illuminated object. If the object reflecting the laser light moves with respect to the incident laser beam, then the speckle pattern moves. Such movement can be used to detect motion. This concept could beneficially be used to detect blood flow. Sometimes the tissue overlying a blood vessel moves slightly as a result of pulsatile blood flow. For example, FIG. 4 shows an imaging system being used to detect blood within a vessel. The imaged vessel and surrounding structures are illuminated with radiant energy produced by a laser, preferably in the near infrared region of the spectrum so relatively deep penetration of the radiant energy occurs, and yet is reflected from red blood cells (RBC); for example, 805 nm light. The reflected radiant energy can be captured by a detector, which is positioned behind an aperture. Thus, any change in the speckle pattern results in a change in the detector's signal output. Any changing speckle pattern is a consequence of RBC movement. If the infrared laser is scanned, then an image of the speckle pattern can be built up and spatially dependent RBC movement can be detected, thus providing a means with which to detect blood vessels. Again, a normally appearing image using white-light illumination could be captured and the blood-vessel movement information could be superimposed on the image.

EXAMPLE 5
Multiphoton Interaction Enhanced Imaging

Under certain irradiation conditions, it is possible to have photons, with a wavelength $\lambda$, interact with an atom or molecule which normally would not absorb at $\lambda$, but which does absorb at a different $\lambda$. For example, fluorescein which has an absorption peak around 500 nm can be induced to fluoresce when irradiated with two photons with a wavelength of 1000 nm, that arrive virtually simultaneously. Three-photon excitation can also be used in certain circumstances, but in this case the wavelength of the photons must be ⅓ that of the wavelength of absorption. This multi-photon effect requires lasers which produce high peak powers (e.g. >2 kW in a pulse length, $\tau_p$<1 ps) and yet have a low average power so that there are no undesirable laser-tissue interactions such as photothermal coagulation. This multi-photon effect can be used for fluorescence imaging as the requisite high photon density can be made to occur only at the focus of the laser beam, which can then be scanned in three dimensions. The benefits of multi-photon excitation is that the incident radiant energy is not attenuated by absorption of the fluorochrome above the plane of focus and the longer excitation wavelengths used are less Rayleigh scattered.

Figure 5:
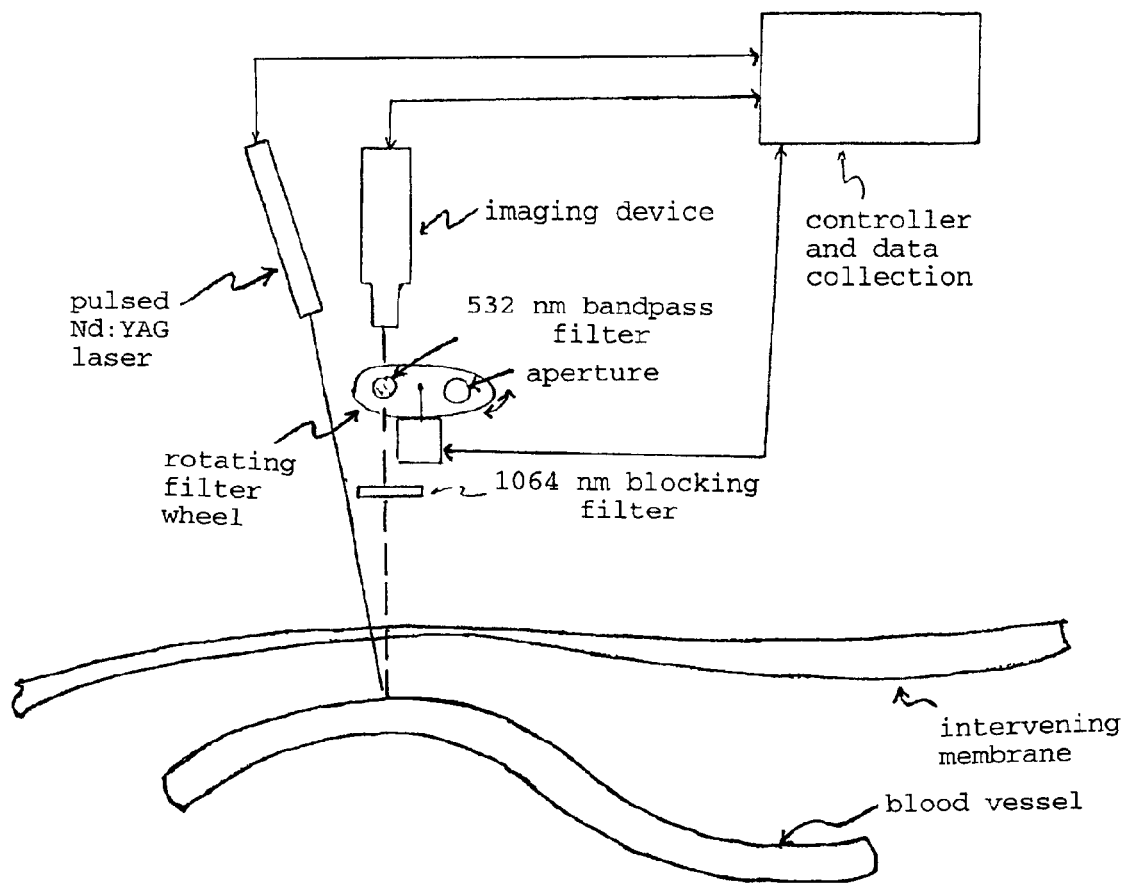
FIG. 5 shows a blood vessel imager where multiphoton effects are used for imaging.

It is generally believed that multi-photon techniques are useful only for fluorescence imaging. However, it is known that the scattering and absorption effects of tissue are related to each other by a mathematical relation from classical electromagnetic theory. Thus, in the electromagnetic spectrum where tissue is highly absorbing, it is also highly scattering. Thus, a multiphoton effect can be used to gather absorption and scattering imaging information. For example, considering that blood absorbs strongly at about 400–425 nm, however radiant energy with this wavelength (which appears blue) is so strongly absorbed in tissue that it only penetrates superficially. However, it is possible with two-photon scattering and absorption to obtain information about blood using radiant energy at 800–850 nm. Such radiant energy is quite penetrating in tissue, and yet will interact with blood if the photon density per unit time is large enough. It is therefore possible to obtain imaging information (FIG. 5) using a pulsed laser producing near infrared radiant energy. For practical reasons, such an imaging scheme may benefit from using a Q-switched Nd:YAG laser (1064 nm), as such lasers are relatively inexpensive and fortuitously blood absorbs strongly at 532 nm. The 532 nm scattered information could be collected in synchrony with the pulsed Nd:YAG laser. On alternate scans, white light or infrared images could be captured. Comparison of the two could be used to determine the location of the blood (or other light absorbing/scattering chromophore) in the field of view.

EXAMPLE 6
Optical Coherence Tomography Enhanced Imaging

Figure 6:
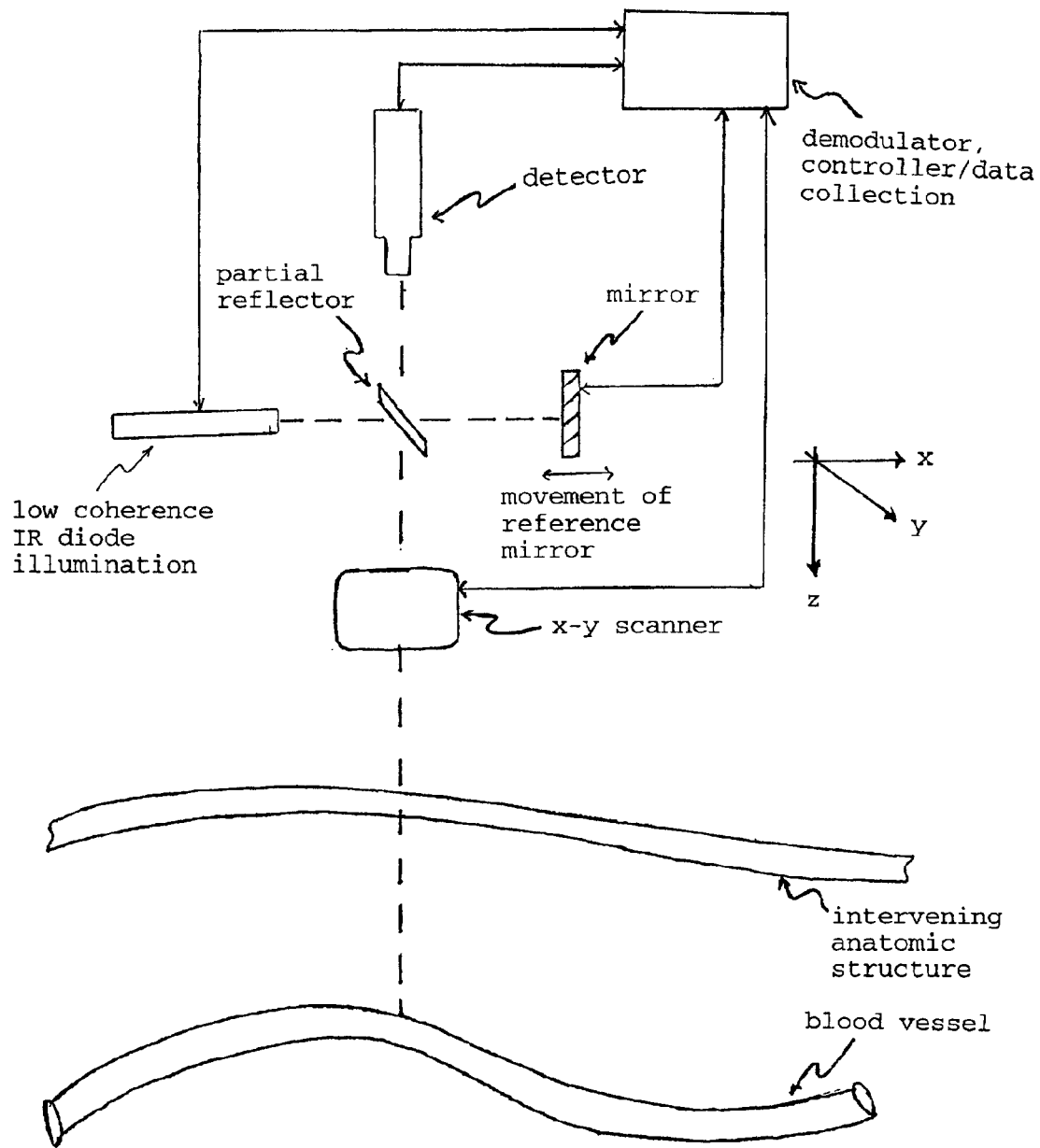
FIG. 6 shows an optical coherence tomographic blood vessel imager.

Optical coherence tomography (OCT) is based on low-coherence interferometry (e.g. white-light Michelson interferometry). High resolution depth-dependent imaging is obtained by focusing light from an optical low coherence source (e.g. LED) on the biological tissue and interfering the backscattered intensities with the incident light (FIG. 6). Images in the first two dimensions are obtained by performing the interferometric measurement as a function of transverse (x,y) positions in the tissue. Third dimension (depth) information in the tissue is collected by varying the reference arm pathlength axially (z position) in the interferometer. Useful interferometric information occurs only when the optical pathlengths of the light traversing the reference path and tissue path are identical to within the coherence length of the source. Optical coherence tomography is beneficial in that is does not require an illumination source with a long coherence length (e.g. a laser) and can be done with the use of optical fibers.

It would be beneficial to use optical coherence tomography with infrared radiant energy to obtain good penetration of the light. By using several wavelengths of light sequentially, in the same manner described for the pulsatile enhanced imaging scheme described previously, specific images of arteries and veins could be obtained, as well as a non-invasive measurement of blood oxygen saturation in a particular imaged vessel.

EXAMPLE 7
Time Correlated Single Photon Counting Enhanced Imaging

Time-correlated single-photon counting (TCSPC) is a statistical technique which may be used to measure the time profile of the emission of a sample following excitation by a short light pulse. The time delay between a trigger ("start") pulse, which is fixed in time with respect to the excitation pulse, and the moment of arrival of a photon emitted by the sample and then detected by a photomultiplier ("stop" pulse) is recorded. By accumulating many such intervals in a histogram, the probability that a photon is emitted by the sample at a certain moment is measured, i.e., the time profile of the emission is measured.

Time-correlated single-photon counting is a commonly used technique in fluorescence spectroscopy due to its wide dynamic range, high time resolution and high sensitivity. Time resolutions of the order of 50 ps (FWHM) are easily achievable with commercial ultrafast laser and detector systems. Typically, a mode-locked argon-ion laser is used to synchronously pump a cavity-pumped dye laser. The resultant train of picosecond pulses may be coupled into an optical fiber in contact with the sample under investigation. The pulse shape changes as it propagates through the medium. This is due to the fact that photon pathlengths are altered through interactions (scattering and absorbing) with the medium. In fact, th e optical properties of the medium may be inferred from the shape of the emitted pulses. Typically, the emitted pulses are collected with an optical fiber positioned on the sample at a known distance from the input fiber. The distal end of the collection fiber is in contact with the detector, which, for ultrafast applications, is a micro channel plate-photomultiplier tube (MAP-PMT).

The optical properties (scattering and absorption) of the material may be obtained through non-linear least squares fitting of the data (amplitude vs. time spectra) to a model function. A diffusion model is commonly used to fit the data. Analytic solutions of the diffusion equation in homogeneous media exist for various simple geometries. This data (absorption and scattering coefficients) can be collected during scanning in the x-y plane in order to build up an image. Depth z dependent information could be obtained using one of the depth discriminate techniques, such as OCT or confocal, described above.

Figure 7A:
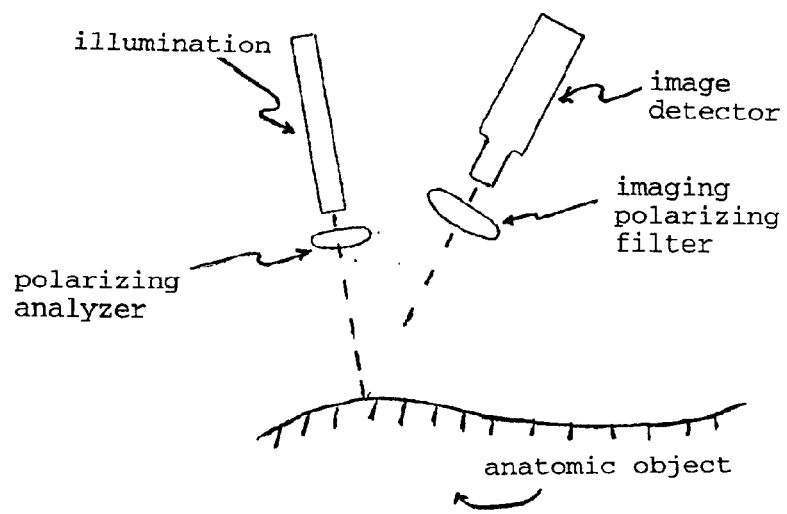
FIGS. 7A–F show various ways in which polarized light and polarizing filters over the detector can be used to enhance blood vessel image contrast.

EXAMPLE 8
Optical Rotatory Dispersion, Circular Dichroism and Polarization Enhanced Imaging Circular dichroism (CD) and optical rotatory dispersion (ORD) are polarization dependent measurements whereby circular dichroism measures a difference between the absorption in matter of radiant energy that is left and right circularly polarized light, while optical rotatory dispersion measures the difference in the refractive indices for left (L) and right (R) circularly polarized light. If a biomolecule is optically active, i.e., if dissymmetric and non-superimposable mirror images of the molecule occur, circularly polarized light interacts with the molecule depending on the handedness of the light. Molecular shape and orientation also determines the degree to which linearly polarized light interacts with a molecule. For example, polarizing sunglasses have absorbing chromophores that are mostly oriented horizontally; thus when light specularly reflected from a roadway (which is, to a degree, linearly polarized with the axis of polarization oriented horizontally), then it is absorbed by the chromophores. Unpolarized light retroreflected from a tissue interface will have a degree of linear polarization; incident linearly polarized light retroreflected (FIG. 7A) from deeper within the tissue will loose the initial polarization, depending on how many scattering events occur within the tissue; the more scattering events that photon experiences, the more the polarization becomes random with respect to the polarization of the injected photon.

Figure 7B:
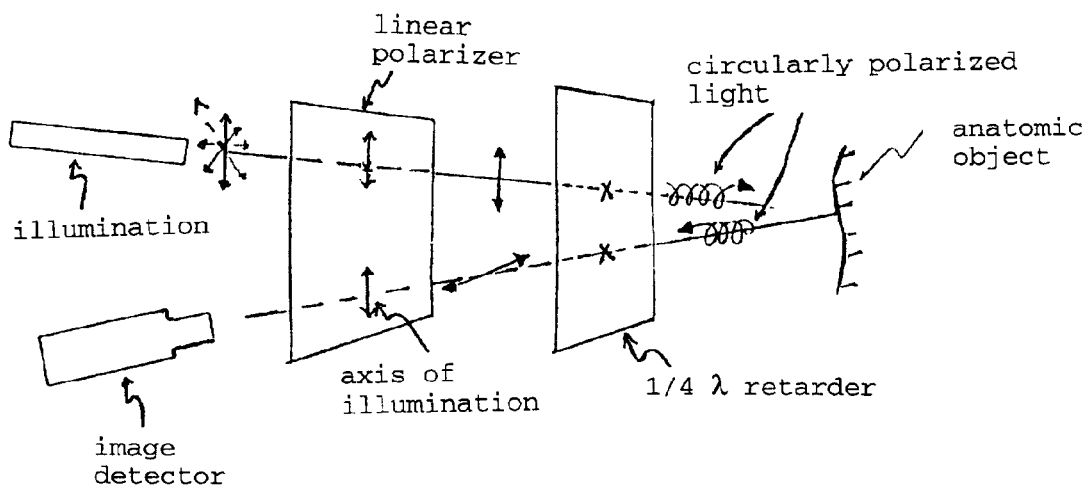

These ideas can be used to improve the ability to image subsurface anatomic structures. For example, specular reflectance from tissue interfaces, which can tend to obscure the image of a subsurface structure, can be reduced or eliminated by linearly polarizing the incident light, and incorporating a linear analyzer whose transmission axis is oriented orthogonal to the transmission axis of the incident light polarizer. Similarly, by passing unpolarized light through a linear polarizer and a wave retarder, circularly polarized light is produced which, when retroreflected, will be absorbed upon passing through the same wave retarder and linear polarizer (FIG. 7B). Note that these polarization techniques which serve to reduce unwanted specular reflection can also be used to increase the ratio of photons scattered once or a few times (i.e. superficially penetrating photons) to photons scattered many times (i.e. deeper penetrating photons). Thus this serves as a way to either reject highly scattered photons which serve to degrade image contrast, or to get depth discriminate information.

These same methods can be used for molecular discrimination. Note that devices to measure the reflectance and absorbance from tissue of polarized light, and the state of polarization in the reflected light, can make use of a photoelastic modulator (PEM), which is a device that, depending on the waveform and phase driving it, can be used to analyze polarized light when used in conjunction with polarizers and waveplates. The frequency at which the PEM is driven, and the frequency of signal detected, also play a role in determining what exactly is being measured (Hinds Instruments, Inc., Oregon).

Figure 7C:
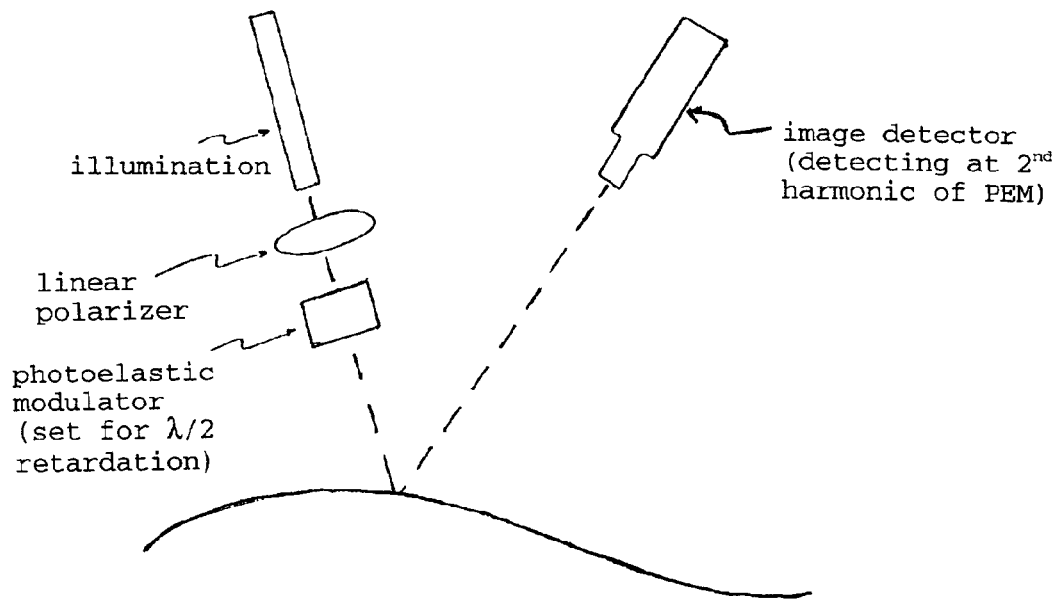
Figure 7D:
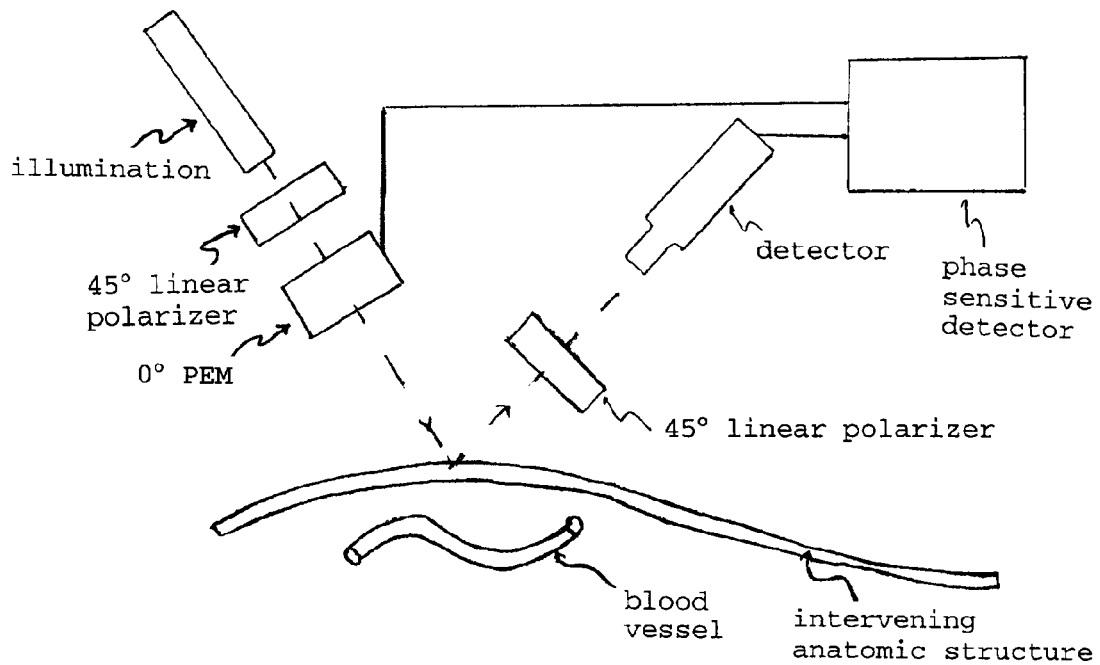
Figure 7E:
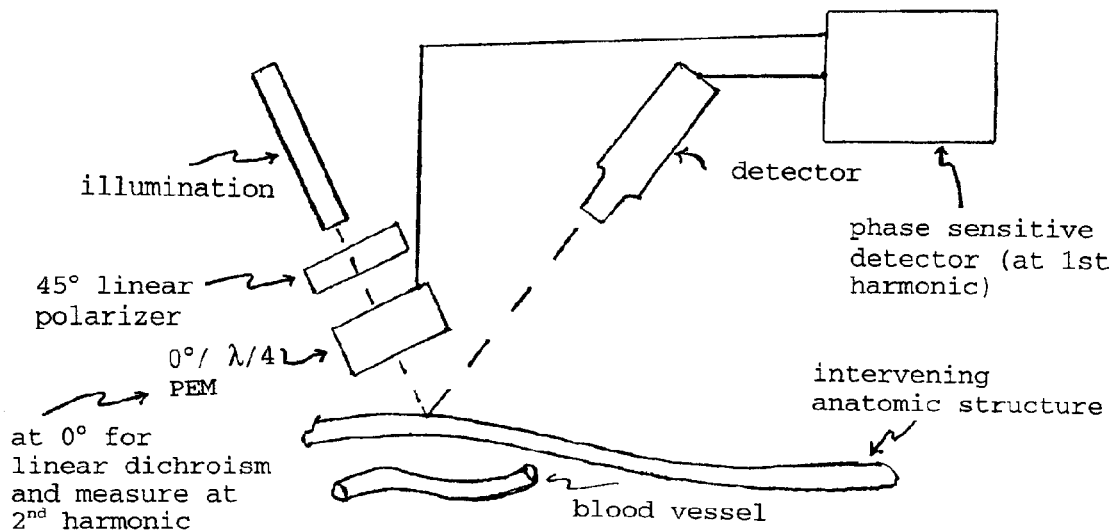
Figure 7F:
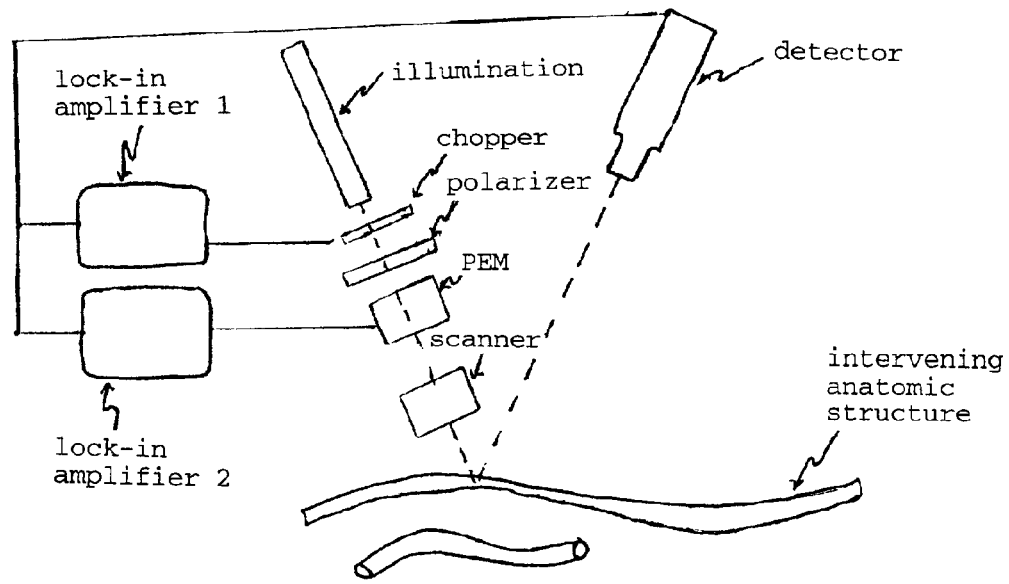

For example, optically active molecules such as glucose can be detected by transmission measurements using CD or optical rotatory dispersion. PM-IRRAS stands for Polarization Modulation Infrared Reflection-Absorption Spectroscopy. It is the differential IR absorption between the s- and p-linearly polarized light for the molecules in a tissue (FIG. 7C). In ellipsometry, the polarization change of a light beam is measured when it is reflected by the sample. This change in polarization is then related to the sample's properties (FIG. 7D). Vibrational circular dichroism (VCD) is the differential absorption between left and right circularly polarized light. It is a measurement of the optical activity for chiral molecules (FIG. 7E). Linear dichroism (LD) is the differential absorption between two orthogonal, linearly polarized states. Linear dichroism is a measurement of the sample's bulk property that is a result of the regular orientation of the molecules in the sample (FIG. 7F with the PEM set at 0° and phase-sensitive detector at the $2^{nd}$ harmonic).

EXAMPLE 9

Image Processing

Image processing devices, which can manipulate digital image data quickly, would be beneficially used in any of the above methods. For example, Hamanatsu Photonic Systems (Bridgewater, N.J.)) sells a unit which can perform real-time edge enhancement, uneven illumination compensation and frame averaging. Alternatively, with the advent of extremely fast video processing hardware, it is possible to perform mathematical operations on the video signals in real-time thereby allowing various enhancement schemes. For example, a Fast Fourier Transform can be performed on the video image, and edge enhancement can be done by high-pass filtering the transform prior to performing the inverse Fast Fourier Transform. One very important post-processing algorithm involves pixel-stretching, whereupon the contrast of a low contrast image is increased by altering the video image pixel values to utilize the full spread of values (e.g. 256) available in the digitizer. As the region-of-interest (ROI) is typically unevenly illuminated, it would b e beneficial to be able to select an ROI on the video monitor, perhaps through the use of a mouse, and to apply the image processing algorithms to that region only. This would maximize the contrast in the region-of-interest and would allow the user to ignore other unimportant information which may be very dark or very light, and so can make automated image processing of the full image difficult.

EXAMPLE 10

Vascular Contrast Enhancement

In order to improve the imaging contrast between blood vessels, or other sub-surface structures, and the surrounding tissue, it may be beneficial to use exogenous chromophores. For example, Indocyanine Green (ICG) is a well know agent which has been used for many years in quantifying cardiac output and imaging retinal vasculature. When dissolved in plasma, it has an absorption maximum at about 800 nm. By employing multiple-wavelength illumination and/or detection whereby one of the images captured was illuminated or detected around 800 nm, and the other at a wavelength where indocyanine green is only weaking absorbing (say, for example, 660 nm), then it is possible to differentially image vasculature. However, when combined with the aforementioned pulsatile imaging methodology, for example, further contrast enhancement will be achieved. This same idea of using exogenous chromophores can be extended with a range of other molecules, some of which have a beneficial tendency of concentrating in diseased tissue. For example, it is know that δ-aminolevulinic acid (δ-ALA) preferentially collects in malignant tissue where it greatly enhances the production of porphyrins. These porphyrins are strongly absorbing and fluorescent, and so this compound combined with the above discussed imaging techniques can be used to identify (and actually treat) cancer.

It could be of importance to provide good contrast between such things as endoscopes, fingertips, other surgical components, etc., in the infrared image. Carbon and graphite, for example, are strong absorbers of near infrared radiant energy. By coating gloves, instruments, etc, in a thin layer of these materials would appear dark in an infrared imaging system.

EXAMPLE 11

Alternating Color and Infrared Imaging and Rapid Sequential Image Display

Most surgeons are most familiar with endoscopic images obtained using white-light illumination and color sensitive cameras. Color information is also used by the surgeon for diagnostic information (e.g. detecting erythema or malignancies). On the other hand, infrared sensitive cameras produce only a black-and-white (B & W) image. It would be beneficial to devise an imaging system whereby the surgeon can either select to quickly change from color to B & W imaging, or to collect the most relevant infrared image information (for example, the location of a subsurface blood vessel) and to superimpose this information on the color image. Another way to achieve the same thing is to use an infrared sensitive CCD detector, in front of which is positioned a rotating filter wheel with red, green, blue and infrared bandpass filters. The filters are positioned in front of the CCD at a known rate and in synchrony with the capture of information from the CCD. The information can then be processed into an infrared image and into a color image (by combining the red, green and blue information).

Another way to enhance the visual appearance of blood vessels in these images is to use a process sometimes referred to, by astronomers, as "blink" imaging. The eye (and brain) are apparently quite sensitive to small changes in the appearance of a visual field, more so than small differences in a static field. It would therefore be beneficial to configure the image processing and display system such that the image would switch rapidly (e.g. 2 Hz) between a white-light illuminated black-and-white or color image and the infrared image. This mode of display would serve to enhance the visualization of the blood vessels.

EXAMPLE 12

Combining with Therapeutic Laser Energy Delivery Devices

Optical fibers can be used to guide the radiant energy of a laser down an endoscope, whereupon it is used to cut, coagulate, or induce fluorescence in tissue. It would be beneficial in certain surgeries, such as third ventriculostomy, to be able to use infrared imaging to identify sensitive subsurface structures such as blood vessels, and then to use the radiant energy produced by a laser (the 2.94 micron wavelength radiation produced by an Er:YAG laser, for example) to produce a fenestration in the membrane (floor of the third ventricle). The use of the imaging technology in conjunction with therapeutic laser radiant energy would be important clinically.

EXAMPLE 13

Coherent Imaging Fiber Bundle

Some of the embodiments of the inventions described will be too bulky to mount on devices that can be easily manipulate by the health-care provider. It might therefore, in certain cases, be beneficial to optically guide the image from a small handpiece over to the image collection and processing device, which could be positioned on a table nearby. Coherent imaging fiber bundles are suitable for this purpose. The input end of the bundle is positioned in the image plane of an optical system directed at the ROI, and the output end of the bundle is positioned in the object plane of the image collection system. This arrangement is light and flexible, thus, gives the health-care provider necessary freedom-of-movement.

EXAMPLE 14

Magnification

Making use of magnification would be a useful addition to the imaging device in many instances. For example, blood vessels in babies are very small and quite difficult to see. Small, telangiectasia vessels are also difficult to see during treatment. The combination of the image contrast improving methods described herein and optical magnification would serve to improve clinical efficiency during blood vessel puncture procedures or treatment of diseased blood vessels.

EXAMPLE 15

Infrared Transillumination

The illumination systems used in the described applications can also be applied as transilluminators. When a beam of light is held against tissues, such as skin or mucous membranes, whether applied externally or internally, much of the light scatters through the tissues and illuminates the area beneath the skin and laterally. This scattered light illuminates tissue structures in proximity to the site where the photons are injected. By using an infrared sensitive detector and infrared incident light or light which has an infrared component, it is possible to observe subsurface anatomic structures such as blood vessels beneath the skin.

EXAMPLE 16

Heads-up and Projection Display

It is typical that the health-care provider needs to keep both hands free for procedures, therefore, any imaging system that is most beneficial is the one that does not need to be hand-held or manipulated. Furthermore, it is of benefit that the imaging system is possible to simultaneously view the actual region of interest on the patient, if it is required that the image of the ROI needs to be displayed for the provider.

In one embodiment of the invention, the video information could be inputted into a video projector whereupon the image of the ROI is projected back onto the actual ROI on the patient. The projected image could be enhanced so that the structures of interest (typically blood vessels) are made as contrasty as possible and the rest of the image is made uniform. Thus the projection would serve to outline the actual position of the structures on the patient, thus enhancing the ease with which they are manipulated by the health-care provider. Another way to achieve a similar effect is to project the video image onto a partial reflecting screen which reflects the image back to the provider; the subject is positioned on the opposite side of the screen so that the video image appears to the provider to be superimposed on the actual subject. This form of display is similar to that used in fighter-aircraft and is sometimes called a heads-up-display.

EXAMPLE 17

Illumination Compensation

Figure 8:
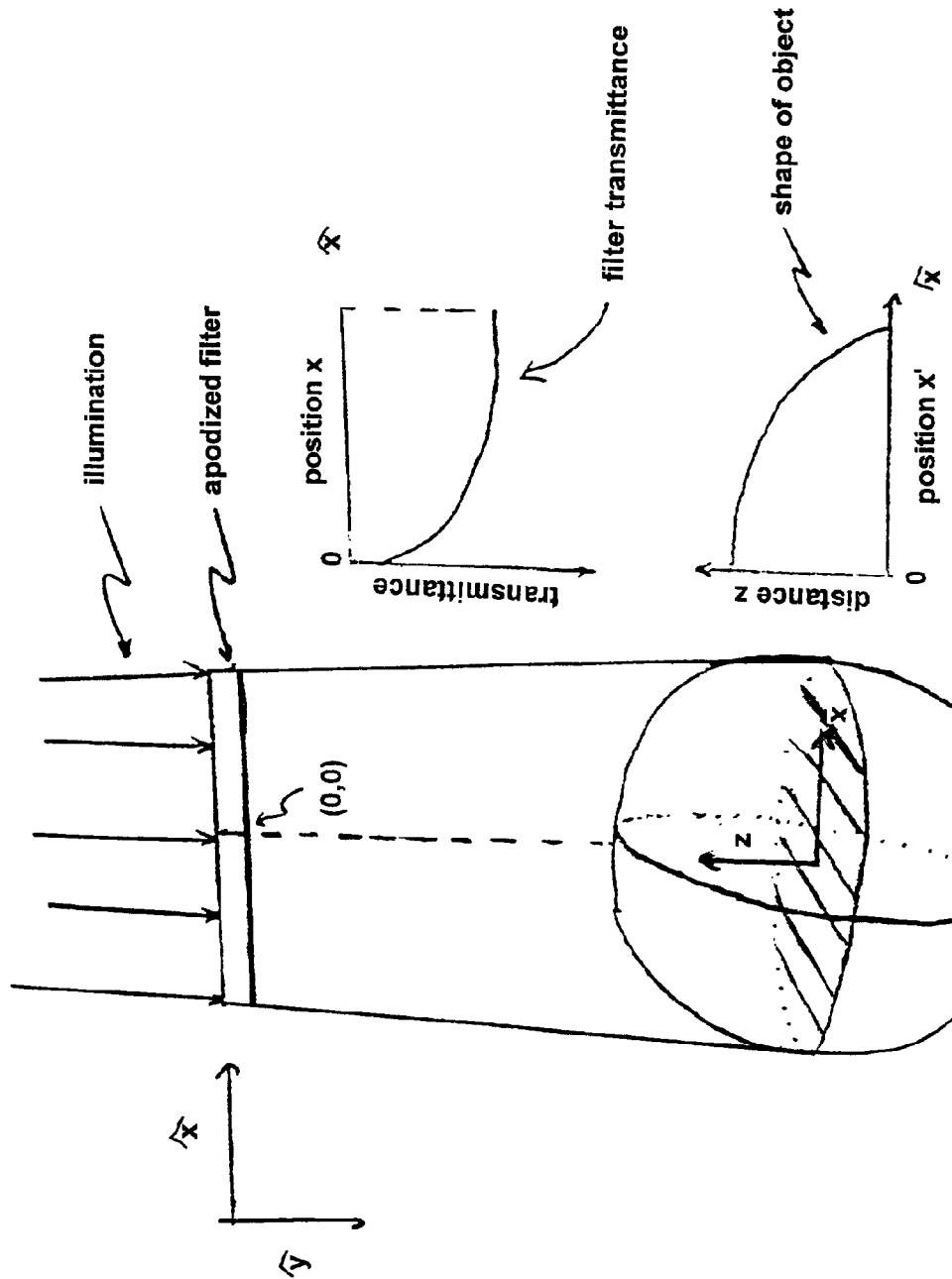
FIG. 8 illustrates one configuration for altering the intensity profile of the incident light to compensate for uneven topography of the imaged anatomic object.

As the dynamic range of CCD video cameras is much less than the human eye, displaying all of the structures of interest in an unevenly illuminated ROIs can be problematic. This problem will be minified by using a camera with a greater dynamic range, such as tube-type cameras. Alternatively, another solution to this is to either tailor the light field to compensate for an uneven topography in the ROI, or to adjust the gain of the CCD pixels non-uniformly. For example, in the case of the former, the addition of anodized mask over the illumination source that has, to a first approximation, a spatially dependent transmittance that is similar to the shape of the ROI (FIG. 8). Another way to achieve the same effect is to control the gain in each pixel of the CCD individually, instead of the typical way whereby they are adjusted together. For example, the healthcare provider could outline an ROI on a video screen with a mouse, and the computer to which the screen is interfaced could then direct information to the CCD video camera such that the gain of the relevant pixels are adjusted, and the rest of the pixels in the image are ignored. A similar sort of non-uniform gain is used in, for example, the Hamamatsu C2400-1 controller which allows the user to adjust the gain of the CCD in four quadrants of the image by adjusting four potentiometers.

EXAMPLE 18

Intravascular Versus Extravascular Blood Discrimination

One problem in surgery and endoscopic surgery is when bleeding occurs, the pooling blood can inhibit the surgeon from visualizing what is below. Unfortunately, this often makes ligating or cauterizing the bleeding vessel difficult to do. The blood flowing out of a vein or artery has a pulsatile flow which is related to the heart beat. The blood pooling in and around the bleeding tissue does not have a pulsatile flow, but instead flows at a steady rate, if at all. Therefore, using the aforementioned pulse imaging concepts would allow the surgeon to remove from an image the absorption due to static blood, and yet still provide imaging information of vascular blood and tissue. In this case, since it may be necessary to differentiate between $HbO_2$, Hb, and Mb, either three different wavelengths of illumination will be necessary, or a rotating filter wheel with three filters may be required.

EXAMPLE 19

Varicose Veins

Figure 9:
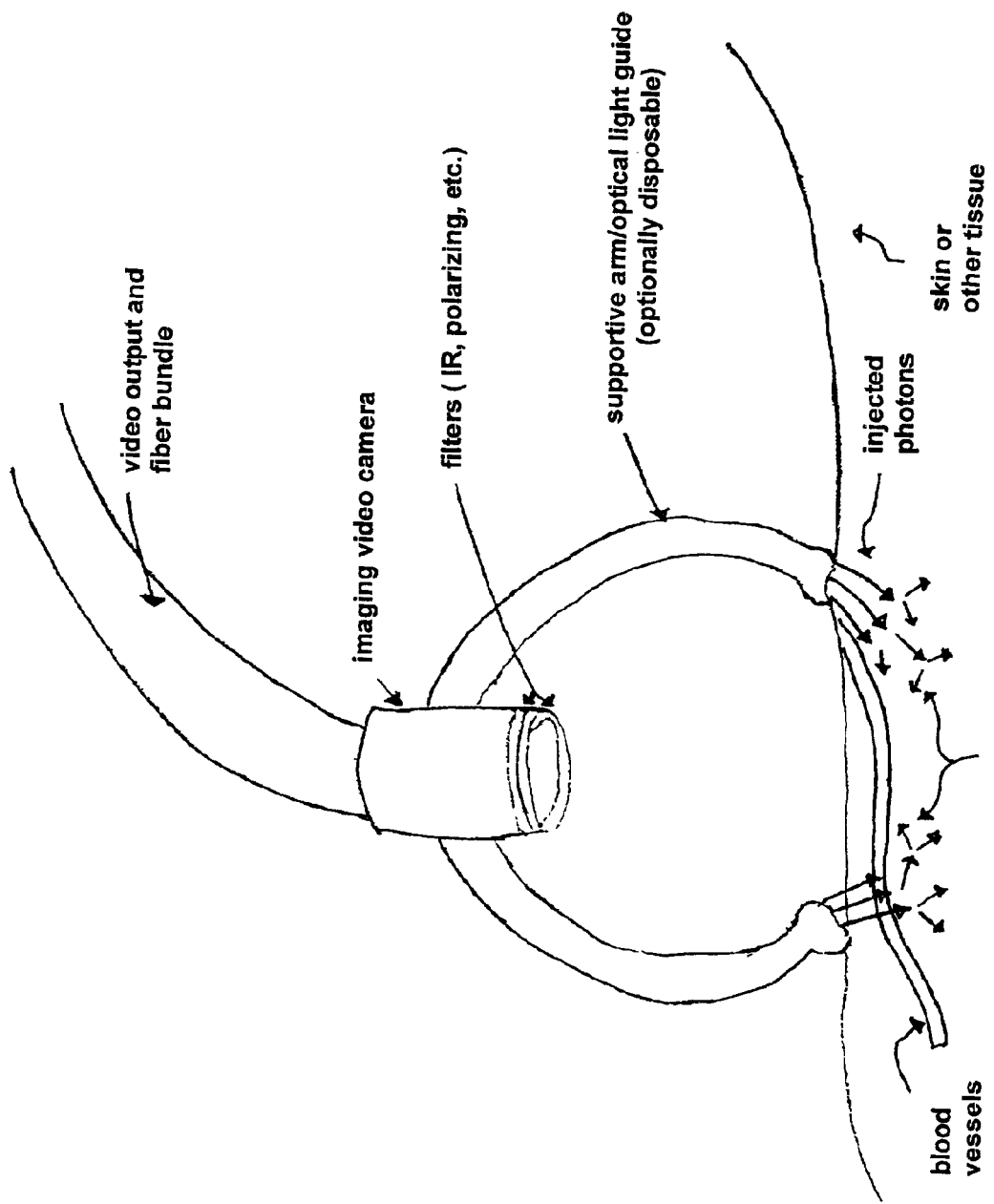
FIG. 9 shows one configuration for a blood vessel viewer including a plurality of arms to hold an illumination source and video detector over the region-of-interest.

Treatment of varicose veins can be problematic in that accurately imaging the vein before and during the procedure can be difficult. Loss of blood from the vein or presence of extravascular blood can further obscure the veins during procedures. The infrared imaging technology described herein would be useful during the therapeutic processes (e.g. vein stripping, laser irradiation, sclerotherapy, etc.) by allowing the surgeon to visualize the vessels accurately (FIG. 9). This device could have a plurality of support arms which serve to allow placement of the device on the patient thus freeing the hands of the surgeon. Alternatively, the device could be positioned on a support employing a ball joint such that it could be positioned in any way by the surgeon and will be kept in that position. The support arms could have incorporated an optical wave guide, such as an optical fiber bundles, which transmits illumination from the source to the surface of the skin. The arms terminate in an infrared filter and optionally a polarizing filter. The light will be directed out of the terminal portion of the arms either perpendicularly to the skin surface, or at an oblique angle directed into the ROI. A video camera can be affixed to the light source such that it images the ROI; the output of the camera is conducted through a cable to the video controller and/or monitor.

In a related surgical strategy, following localization of the vessels by these and other methods not described here, varicose veins may be treated by intraluminal insertion of an optical fiber which guides laser radiant energy (e.g. Nd:YAG 1064 nm radiation) into the vessel and inducing coagulation. This procedure would further be improved as the fiber could be coated in an infrared absorbing agent (such as ICG) whereby it could be imaged with the technology discussed herein.

EXAMPLE 20

Endoscopic Surgery

Endoscopic surgery, such as a third ventriculostomy, would benefit from the technology described herein. It is always important for the endoscopic surgeon to avoid dissecting blood vessels during insertion and advancement of the endoscope. The infrared imaging technology and other blood discrimination techniques described herein would be of benefit in allowing the endoscopist to avoid such vessels.

EXAMPLE 21

Localizing Blood Volumes for Analytical Spectral Measurements

Measuring analyte levels in blood or other tissues with minimally invasive techniques is a very desirable objective. A problem encountered during optical spectral measurements of blood analyte levels is the inability to measure the volume of tissue interrogated. This problem is further compounded by the fact that differences may exist between analyte concentrations extravascularly versus intravascularly. These differences may be difficult to differentiate, resulting in skewed values. The vessel imaging technology described herein allows for the blood in a vessel to be identified. In other words, the blood can be located. Thus, in effect, a virtual optical isolation of a volume of blood may be performed. Once the volume is isolated in this way, the available spectral analysis techniques could be further employed to obtain the information of interest regarding analyte concentration, or regarding any blood disorders that are characterized by unique spectral shifts.

EXAMPLE 22

Disposables

To maintain sterility or at least to keep anything from being positioned near or on a patient, it would be beneficial to employ a disposable shield in many of the aforementioned methods such that any biological material (blood, saliva, ablated tissue, etc.) could not contaminate the imaging process. For example, a disposable plastic sheath that covers the objective lens, scanner and/or camera of the imaging system would be useful. The contact probe illustrated in FIG. 9 could itself be disposable. Alternatively, disposable plastic sheaths could be also employed on each of the components that actually touches the patient.

EXAMPLE 23

An infrared sensitive CCD video camera (e.g. Hamamatsu C2400-79, Hamamatsu Photonic Systems, Bridgewater, N.J.) and an image processing and analysis system (Hamamatsu Argus-20) are coupled together. A 250 W quartz incandescent light source is optically coupled into a light transmitting fiber bundle which is coupled to an endoscope (e.g. Smith & Nephew Dyonics No. 3626S focusing video arthroscope). The proximal end of the endoscope is connected to a custom-made coherent fiber optic bundle (Schott Fiber Optics, MA) which carries the imaging information to the infrared camera. Between the fiber bundle and infrared camera is located an infrared long-pass filter (e.g. Edmund Scientific RG715 glass filter, Edmund Scientific, Barrington, N.J.). A macrolens on a c-mount, attached to the CCD camera, is used to image the end of the fiber bundle. The image processing unit is set to enhance edges and frame average in order to minimize the appearance of noise in the image.

EXAMPLE 24

An infrared sensitive CCD video camera (e.g. Dage-MTI CCD 300) was fixed with a 19–38 mm zoom lens and the output was sent to a standard video monitor. An optical infrared long-pass filter (Edmund Scientific, Inc.) was positioned in front of the lens of the video camera. The device was used to image the varicose veins of a patient undergoing surgical removal of the veins. The (epi-) illumination was optionally a 30 W quartz camcorder light source, which had a Kodak Wratten No. 29 (red) gelatin filter placed in front of the source, or a white-light source (Smith and Nephew, Inc.) connected to an endoscope, which was interstitially positioned within the patient's leg below the varicose veins in order to provide back-illumination of the veins. During this experiment, it was determined that the greatest vein-tissue contrast was achievable when the black-level control on the CCD camera controller was minimized, and the gain was then adjusted in order to obtain a visible image on the video monitor. The veins were imaged well with either interstitial transillumination, or red-filtered epi-illumination. It was also determined that by using an oblique (non-normal) viewing angle and/or oblique illumination angle, the contrast of the blood vessels was enhanced.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of optically imaging subsurface anatomic structures and biomolecules in an individual or animal comprising:

illuminating a region of interest with light having a wavelength from the red to radiant infrared region of the light spectrum via a light source;

detecting red and infrared light from said region of interest with a red and infrared light sensitive image detector;

enhancing said detected image via pulsatile enhanced imaging, confocal enhanced imaging, Raman enhanced imaging, laser speckle enhanced imaging, multiphoton interaction enhanced imaging, optical coherence tomography enhanced imaging, time correlated single photon counting enhanced imaging, optical rotary dispersion image, circular dichroism imaging or polarization enhanced imaging;

transmitting said enhanced image to a video monitor external to said image detector; and displaying said enhanced image on the video monitor thereby optically imaging subsurface anatomic structures and biomolecules.

2. The method of claim 1, wherein said wavelength is about 600 nm to about 1100 nm.

3. The method of claim 1, wherein said detected red and infrared light is transmitted light, reflected light, absorbed light, or emitted light.

4. The method of claim 1, further comprising: adding an exogenous chromophore to the region of interest.

5. The method of claim 4, wherein said chromophore is indocyanine Green (ICG) or d-aminolevulinic acid.

6. The device of claim 1, wherein said light is a light-emitting diode (LED) filtered with a bandpass filter, a diode laser or filtered broadband illumination.

7. The device of claim 1, wherein said image detector is a charge-coupled device (CCD) or a CCD video camera.

* * * * *